US00PP32607P2

(12) United States Plant Patent
van Langen

(10) Patent No.: US PP32,607 P2
(45) Date of Patent: Dec. 8, 2020

(54) ***ECHEVERIA* PLANT NAMED 'TSAECH1910'**

(50) Latin Name: *Echeveria agavoides*
Varietal Denomination: TSAECH1910

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/873,491

(22) Filed: Apr. 21, 2020

(30) Foreign Application Priority Data

Sep. 12, 2019 (QZ) ..... PBR 2019/2218

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* plant named 'TSAECH1910' which is characterized by an abundance of narrowly oblanceolate, dark yellow-green foliage that is tightly held in a compact stemless rosette, foliage that becomes progressively suffused with dark greyed-purple on the abaxial surface, foliage that is distally margined and tipped with dark greyed-purple on the adaxial surface, and the stability of these characteristics from generation to generation.

4 Drawing Sheets

Latin name of the genus and species: The Latin name of the genus and species of the novel variety disclosed herein is *Echeveria agavoides.*

Variety denomination: The inventive variety of *Echeveria* disclosed herein has been given the variety denomination 'TSAECH1910'.

CROSS REFERENCE TO RELATED APPLICATIONS

This application claims priority to the Community Plant Variety Rights application number 2019/2218, filed Sep. 12, 2019, which is herein incorporated by reference.

BACKGROUND OF THE INVENTION

Parentage: 'TSAECH1910' is a seedling selection resulting from the open pollination of a plurality of cultivated unnamed *Echeveria agavoides* plants (not patented) In the spring of 2014, seed harvested from said *Echeveria agavoides* plants was sown at a commercial greenhouse in Heerhugowaard, the Netherlands and allowed to grow to maturity for observation. In the summer of 2015, one seedling resulting from the open pollination was observed to exhibit unique growth and foliage characteristics and was isolated for further evaluation in order to confirm the distinctness and stability of the characteristics first observed. Upon confirmation of distinctness and stability, 'TSAECH1910' was selected for commercialization.

Asexual Reproduction: Asexual reproduction of the new cultivar 'TSAECH1910', by way of rooting leaf cuttings, was first initiated in the spring of 2016 at the inventor's commercial greenhouse in Heerhugowaard, the Netherlands.

Through four subsequent generations, the unique features of this cultivar have proven to be stable and true to type.

SUMMARY OF THE INVENTION

The cultivar 'TSAECH1910' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1910'. These characteristics in combination distinguish 'TSAECH1910' as a new and distinct *Echeveria* cultivar:

1. 'TSAECH1910' exhibits an abundance of narrowly oblanceolate succulent foliage which is tightly held in a compact, stemless rosette; and
2. 'TSAECH1910' exhibits dark yellow-green foliage that is slightly to moderately glossy; and
3. 'TSAECH1910' exhibits an adaxial foliage surface which is distally margined and tipped dark greyed-purple; and
4. 'TSAECH1910' exhibits an abaxial foliage surface which becomes progressively suffused with dark greyed-purple towards the apex.

BOTANICAL DESCRIPTION OF THE PLANT

Figure 1:
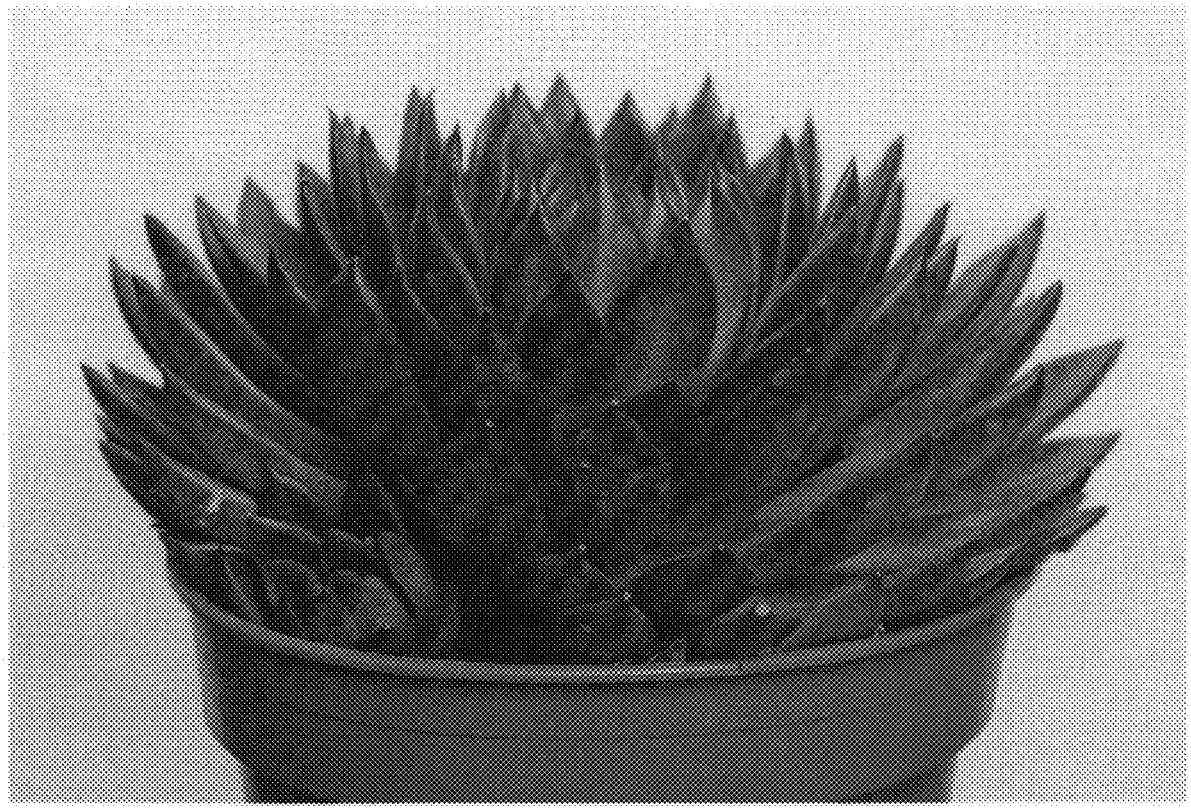
FIG. 1 illustrates, as nearly true as it is reasonably possible to make the same in color photographs of this type, an exemplary plant of 'TSAECH1910' grown in a commercial greenhouse in Heerhugowaard, the Netherlands. This plant is approximately 12 months old, shown planted in an 17 cm container.
Figure 2:
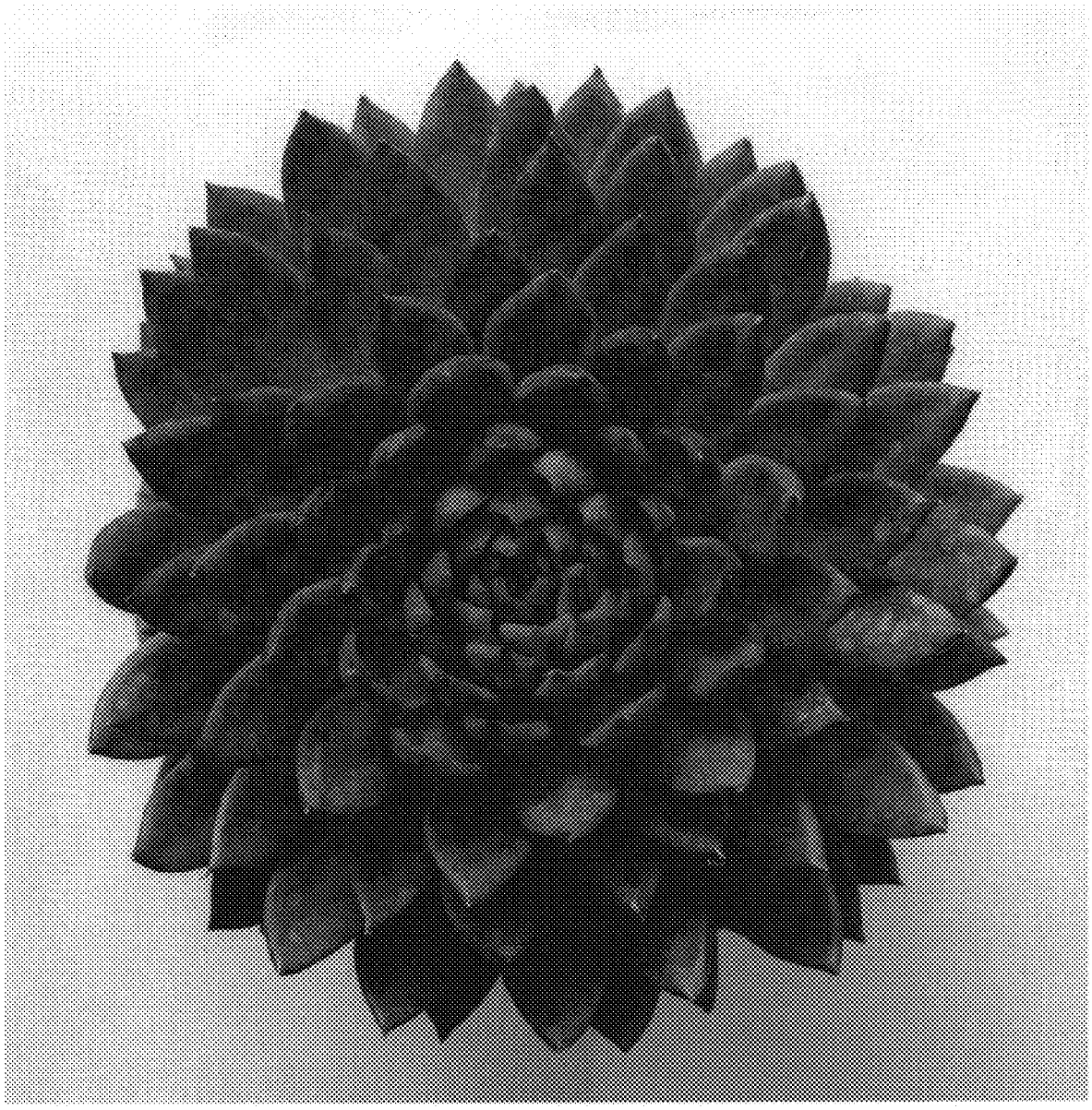
FIG. 2 illustrates, as nearly true as it is reasonably possible to make the same in color photographs of this type, the typical foliage arrangement of 'TSAECH1910'.
Figure 3:
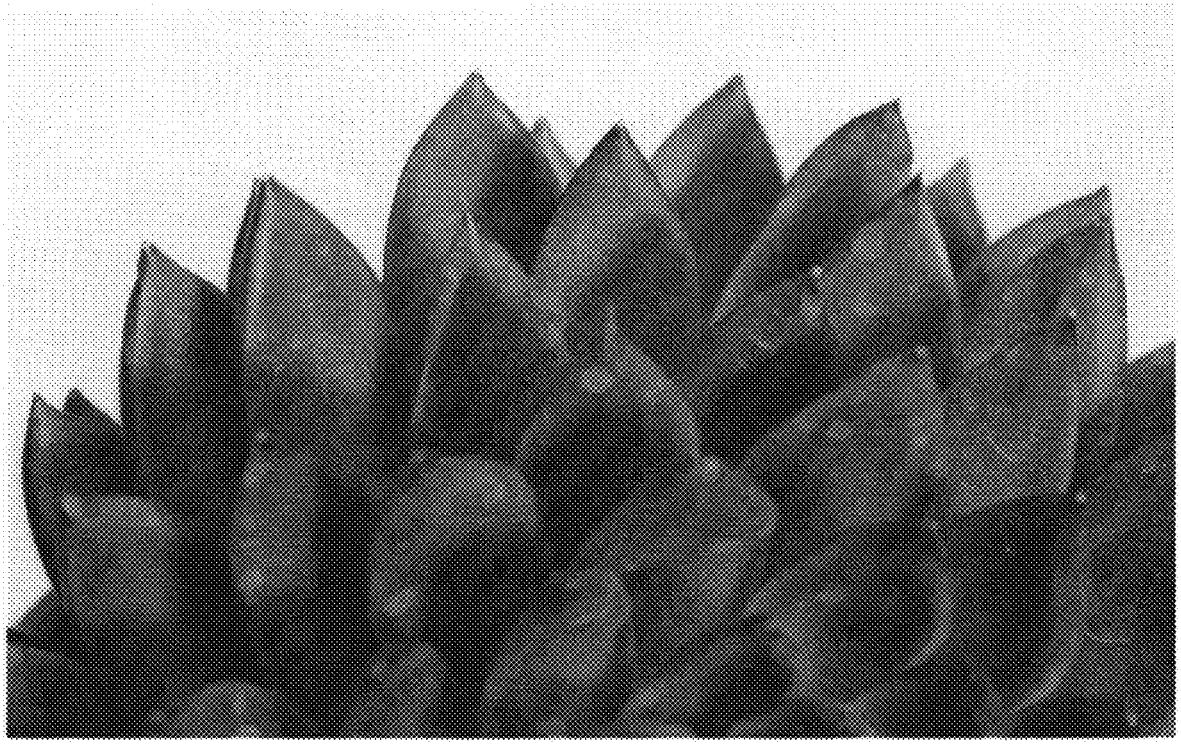
FIG. 3 illustrates, as nearly true as it is reasonably possible to make the same in color photographs of this type, the adaxial surface of the juvenile and mature foliage of 'TSAECH1910'.
Figure 4:
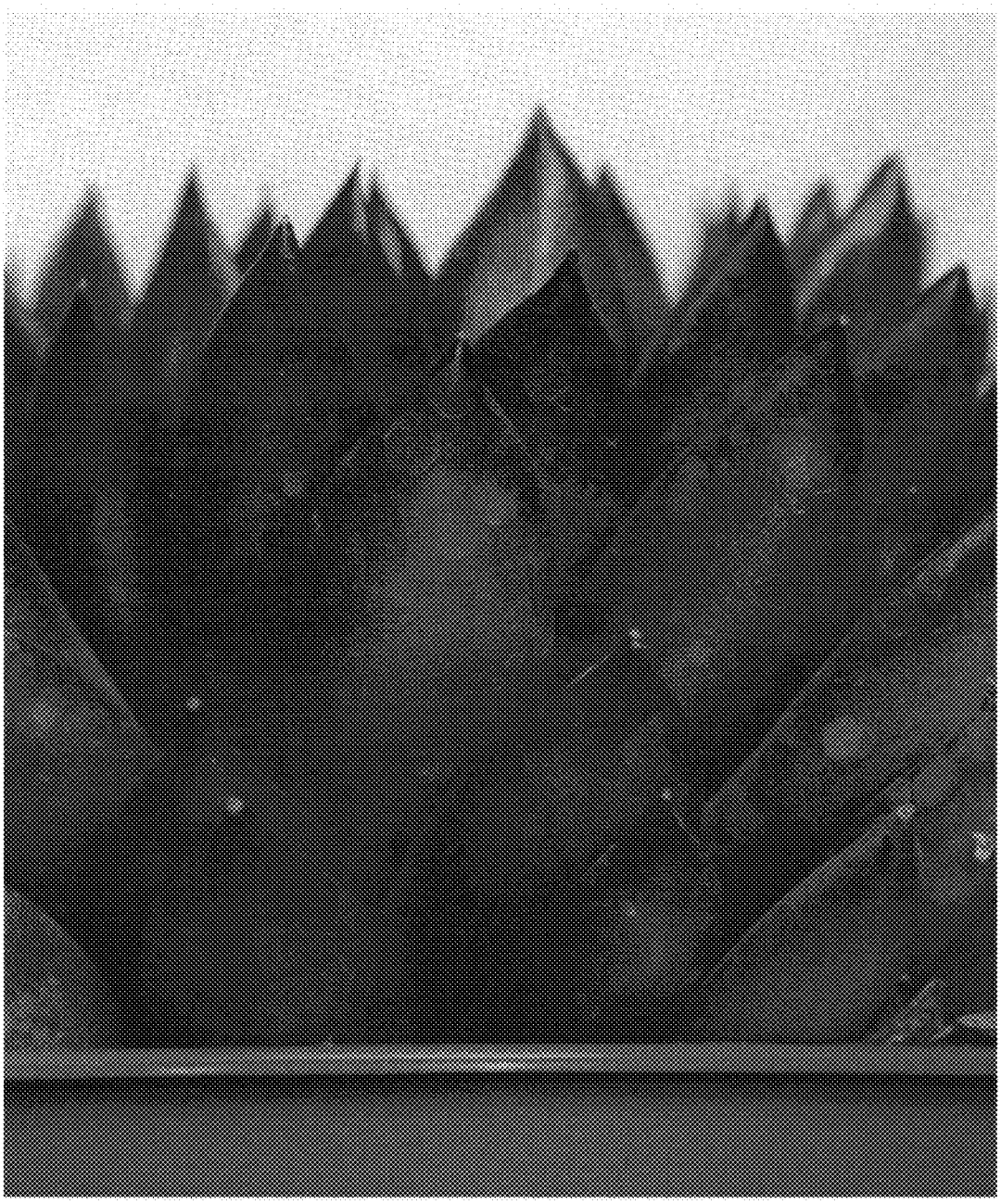
FIG. 4 illustrates, as nearly true as it is reasonably possible to make the same in color photographs of this type, the abaxial surface of the mature foliage of 'TSAECH1910'.

The following observations and measurements made in January of 2020 describe averages from a sample set of six specimens of 12 months old 'TSAECH1910' plants grown in 17 cm nursery containers at a commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1910' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1910' and comparisons with the parent plants and closest known comparator are provided below.

Plant description:

*Growth habit*.—Succulent perennial with foliage growing in a stemless basal rosette.

*Plant shape*.—Flattened.

*Height from soil level to top of foliar plane*.—10.5 cm.

*Plant spread*.—Average of 19.6 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in an 11 cm container.

*Disease and pest resistance or susceptibility*.—More resistant to insect pests known to infest *Echeveria* spp.; no more or less tolerant or resistant to pathogens known to infect *Echeveria* spp.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 150 leaves per rosette.

*Shape*.—Oblong to slightly oblanceolate.

*Dimensions*.—8.0 cm long, 2.3 cm wide, and 0.9 cm thick, on average.

*Aspect*.—Very slightly concave and slightly curved upwards.

*Attitude*.—Both juvenile and mature foliage are held upright at an average angle of 20 degrees from vertical; innermost whorls are held more upright while outermost whorls are slightly more relaxed.

*Apex*.—Apiculate.

*Base*.—Long cuneate.

*Margin*.—Entire; not undulated.

*Pubescence, texture and luster of the adaxial surface*.—Glabrous and smooth; slightly glossy with the exception of the proximal portion towards the base which is moderately glossy; moderately glaucous.

*Pubescence, texture and luster of the abaxial surface*.—Glabrous, smooth, and moderately glossy.

*Color*.—Juvenile foliage, adaxial surface — Nearest to in between green and greyed-green, RHS 138A and 191A, and fading to a lighter shade of yellow-green towards the base, nearest to RHS 145A; tipped greyed-purple, nearest to RHS 183D; the epicuticular wax covering the leaf surface is greyed-green, nearest to RHS 198B. Juvenile foliage, abaxial surface — Nearest to in between yellow-green and greyed-green, RHS 191B and 191A, and fading to a lighter shade of yellow-green towards the base, nearest to RHS 148D; tipped greyed-purple, nearest to RHS 183D. Mature foliage, adaxial surface — Nearest to in between yellow-green and green, RHS 147B and 137B, and fading to a lighter shade of yellow-green towards the base, nearest to in between RHS 148C and 148D; distally margined and tipped greyed-purple, nearest to RHS 187A; the epicuticular wax covering the leaf surface is greyed-green, nearest to RHS 198B. Mature foliage, abaxial surface — Yellow-green, nearest to in between RHS N148B and N148C, and fading lightly towards the base, nearest to RHS N148D, and becoming progressively more suffused with greyed-purple towards the apex, nearest to a mixture of RHS N186C and 187A.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1910' differ from the parents, unnamed and unpatented *Echeveria agavoides* plants, in the following characteristics described in Table 1 below.

TABLE 1

| Characteristic | 'TSAECH1910' | Unnamed *Echeveria agavoides* plants. |
|---|---|---|
| Foliage width. | Narrower than the parents. | Broader than 'TSAECH1910'. |

TABLE 1-continued

| Characteristic | 'TSAECH1910' | Unnamed *Echeveria agavoides* plants. |
|---|---|---|
| General coloration of the foliage. | Darker yellow-green and more heavily suffused with greyed-purple on the abaxial surface. | Lighter yellow-green, and more lightly suffused with greyed-purple on the abaxial surface. |

COMPARISONS WITH THE CLOSEST KNOWN COMPARATOR

Plants of the new cultivar 'TSAECH1910' differ from the closest known commercial comparator, the common form of the species *Echeveria* 'Sagitta' (U.S. Plant Pat. No. 26,231), in the following characteristics described in Table 2 below.

TABLE 2

| Characteristic | 'TSAECH1910' | 'Saggita' |
|---|---|---|
| Foliage width. | Narrower than 'Saggita'. | Broader than 'TSAECH1910'. |
| General coloration of the foliage. | Darker yellow-green and more heavily suffused with greyed-purple on the abaxial surface. | Lighter yellow-green, and more lightly suffused with greyed-purple on the abaxial surface. |
| General coloration of the adaxial foliage margins, | More broadly and conspicuously margined with greyed-purple. | More narrowly and inconspicuously margined with greyed-purple. |

That which is claimed is:

1. A new and distinct variety of *Echeveria* plant named 'TSAECH1910', substantially as described and illustrated herein.

* * * * *